United States Patent
McLaughlin et al.

(10) Patent No.: US 6,891,605 B2
(45) Date of Patent: May 10, 2005

(54) MULTIMODE SAMPLE INTRODUCTION SYSTEM

(76) Inventors: Roger Louis Joseph McLaughlin, 3700 Marlborough Place, Niagara Falls (CA), L2J 2S5; Ian David Brindle, 18 Norris Place, St. Catharines (CA), L2R 2U8

( * ) Notice: Subject to any disclaimer, the term of this patent is extended or adjusted under 35 U.S.C. 154(b) by 27 days.

(21) Appl. No.: 10/445,933

(22) Filed: May 28, 2003

(65) Prior Publication Data

US 2003/0230712 A1 Dec. 18, 2003

Related U.S. Application Data

(60) Provisional application No. 60/383,103, filed on May 28, 2002.

(51) Int. Cl.[7] .................................................. G01N 1/00
(52) U.S. Cl. ........................ 356/36; 356/315; 356/316; 250/288
(58) Field of Search .......................... 356/36, 312, 315, 356/316, 417; 250/288

(56) References Cited

U.S. PATENT DOCUMENTS 5,939,648 A   8/1999   Phan

Primary Examiner—F. L. Evans
(74) Attorney, Agent, or Firm—Eli D. Eilbott

(57) ABSTRACT

An apparatus for determining one or more elements or compounds in a laboratory sample, and for simultaneously performing both vapor generation and nebulization in one device, is disclosed. The apparatus comprises an enclosed cyclonic spray chamber with two integrally affixed cylindrical ports, one for introducing a nebulizer into the chamber and the other for facilitating volatilization of analytes within the chamber. In addition, two conical tubes are integrally affixed to the chamber and oriented opposite each other, with one tube serving as the means for introducing a sample into the spray chamber, and the other tube serving as the means for introducing reductant/reactant into the spray chamber. This invention allows a sample that has been introduced into the spray chamber to be subjected to nebulization or vapor generation, or to both processes.

5 Claims, 4 Drawing Sheets

MULTIMODE SAMPLE INTRODUCTION SYSTEM

NOTE: Applicants claim for this Application the priority filing date of May 28, 2002 for Provisional Patent Application No. 60/383,103.

BACKGROUND AND DESCRIPTION OF INVENTION

1. Field of the Invention

The present invention, entitled "Multimode Sample Introduction System," is an apparatus for use in the field of scientific laboratory analysis. More particularly, the present invention relates to a combined spray chamber/gas-liquid separator for use in introducing samples into devices to measure elemental concentrations by atomic spectrometry.

2. Description of Related Technology

Atomic spectrometry is a technique that is applied to the determination of elemental concentrations whereby solutions of the species to be determined are delivered ultimately as atoms or ions in the gas phase where their concentrations are measured as a result of one of several physical processes. The principal methods of analytical atomic spectrometry include atomic absorption, atomic emission, atomic fluorescence and mass spectrometry. Commercial instruments are available for the determination of elemental concentrations by all four of the methods mentioned above.

Efficient delivery of the aqueous sample for determination of the elements has been a challenge for the atomic spectroscopy community and thus sample introduction has been described as the "Achilles' heel of atomic spectroscopy." Analytical Chemistry, Vol. 56, pp. 787A–798A (1984). The principal reason for the problem arises from the need to deliver droplets of solution of a small diameter into the instrument. A consequence of the segregation of larger droplets is that a small portion only of the solutions (typically less than 5%) is delivered to the instrument. The remaining 95% is usually pumped to waste.

The concentrations of several elements in water, for example, are mandated by environmental regulation to be held at very low levels, which are difficult to measure accurately by most techniques. In metallurgical applications, the presence of some elements, such as germanium, bismuth and arsenic, alter important properties of metals and can improve or diminish advantageous characteristics of those metals and hence are regulated by industry standards.

Devices and methods for measuring and analyzing the concentration of elements and chemical compounds present in laboratory samples are well-known in the art. Among the preferred techniques for the determination of low levels of elements is the technique of vapor generation, in which a dissolved species, such as arsenic, in an ionic form, can be transformed into a species that is volatile. Such a form of the element can partition between the solution and the gas phase. In general, vapor generation involves the use of a gas-liquid separator for sample introduction purposes where certain analyte elements or compounds of interest are chemically converted into a vapor phase and the resulting vapor phase species are then stripped out of solution and delivered in the gaseous form. Although there are several volatile species that can be generated for this type of measurement from the vapor phase, the major species are hydrides, generated by the reaction of the ionic species in the aqueous solution. While vapor generation is limited in terms of the range of elements that are amenable to such a process, it provides significantly greater analyte transfer efficiency as compared to conventional nebulization (discussed further below).

Vapor generation has a long history. The first vapor generation test was developed by Marsh in the 1830s and was used for the determination of arsenic in cases of poisonings. Dedina, J. and D. L. Tsalev, *Hydride Generation Atomic Absorption Spectrometry* (1995). The sensitivity of the test persuaded researchers to use it to determine arsenic and later antimony in a variety of matrices. The vapor generation test for arsenic involved the reduction of arsenic to arsine in an acidic solution containing dissolving zinc. Researchers noted interferences from transition elements, and various techniques to minimize such interferences were reported during the early years following the development of the test.

The major advantage of the vapor generation technique was the separation of the analyte, in gaseous form, from the matrix. In the 1990s, the efficiency of removal of the analyte from solution was determined to be greater than 95 percent. Le, X. C., et al., 258 *Anal. Chim. Acta*, 307 (1992). From the first report, when Holak determined arsenic after cryotrapping, followed by flame atomic absorption spectrometry, improvements in detection limits were noted. Holak, W., 41 *Anal. Chem.* 1712 (1969). Since a limited number of analytes were transformed into volatile species, another benefit of vapor generation was realized when spectral interferences from line-rich elements (e.g., iron) were eliminated from the atom source.

Over a period of years, mercury, germanium, tin, selenium and tellurium were added to the list of analytes determined to be amenable to vapor generation. Dedina, supra. More recently, in particular over the last two decades, the list of elements that can be determined by being transformed into vapor phase species has grown considerably. Lead, cadmium and thallium were determined from their hydrides, nickel was determined by transforming it into its tetracarbonyl, and osmium was determined from its volatile oxide. Within the last five years, several more elements, including Ag, Au, Co, Cr, Cu, Fe, Mn, Ni, Pd and Rh, were added to the list of elements that can be determined from volatile species. While it is not clear in what form some of these elements are delivered to the excitation source, it is clear that mass transfer efficiencies are significantly greater than those from solution nebulization.

All of the foregoing advantages aside, vapor generation has often proved difficult and problematic. Problems identified by various researchers include the following: poor reproducibility of results (i.e., high relative standard deviations (RSDs)); need for separate introduction systems for vapor generation and nebulization; limited number of analytes amenable to such processing; complex chemistry; transfer-line problems (e.g., condensation, catalytic decomposition of species); difficulty of understanding mass transfer processes from the gas-liquid separator; and complicated nature of the chemistry of vapor generation and interferences. For example, gas-liquid separators commonly encounter the problem of elevated RSDs, due to the nebulization of solution during the vapor generation reaction, which causes the formation and bursting of bubbles of hydrogen (or of carrier gas, in the case of frit-based and similar systems). Such effervescence entrains droplets into the gas stream, which, in turn, can give rise to uneven and unpredictable spikes in concentration of volatile species.

Numerous inventions over the last 35 years have sought to improve the delivery of elements into the vapor phase. Many devices produce noisy signals in the instrument, thereby reducing the efficiency of the measurement and making it more difficult to measure very low concentrations. Most devices (usually called gas-liquid separators) depend upon the generation of a gas, usually hydrogen, in the solution, which strips the volatile species from solution. Such devices use a reagent (usually a solution of sodium borohydride $NaBH_4$), which mixes with an acidified solution of the sample and generates both the vapor phase species and hydrogen simultaneously.

A variety of gas-liquid separators has evolved over the years. Holak's approach was to trap the generated hydride in a U-tube cooled with liquid nitrogen and subsequently desorb it. Holak, supra. In addition, the Thompson U-tube and various frit-based separators have been described over the years. Dedina, supra. One recurring issue is the "dead volume" of the gas-liquid separator. Perkin-Elmer developed two devices that are useful for reducing such dead volume. Brindle and Zheng compared several designs for gas-liquid separators for the determination of mercury, including a model detuned nebulizer (i.e., one with poor nebulizing properties). Brindle, I. D. and S. Zheng, "A Comparison of Gas-Liquid Separators for the of Mercury," 51 *Spectrochimica Acta, Part B*, pp. 1777–80 (1996). CETAC Technologies, Inc. developed a gas-liquid separator that uses a glass post onto which the premixed reaction mixture is pumped. A tangential flow of argon is used to strip the volatile species as the liquid flows along the post.

Another methodology for determining the level or concentration of one or more chemical compounds or elements in a laboratory sample is nebulization, which typically involves use of a cyclonic spray chamber to atomize or aerosolize the target solution into tiny droplets that become briefly suspended in said chamber. In short, nebulization is a process whereby a solution is transformed into an aerosol. This nebulization process is most frequently achieved by passing high velocity gas past or over a capillary that carries a solution. The liquid is propelled into the gas phase as droplets of various sizes. The diameter of the droplets is a function of the design of the nebulizer and the flows of gas and solution into it. A second device, usually called a spray-chamber, is used in atomic spectrometry to segregate the finer particles (usually particles of a size less than approximately 10 micrometers) from the larger particles, which are allowed to coalesce and be drained away. The small droplets are carried by the gas flow to the atomic spectrometry instrument.

It has been demonstrated that the introduction of a nebulized solution of potassium chloride simultaneously with vapor generated species results in a significant increase in signal of volatilized species from the sample. Brindle, I. D. and X-C. Le, 61 *Anal. Chem.* 1175 (1989). In such circumstances, the potassium served to enhance the signal from the analytes by the so-called easily ionized element effect.

In the late 1990s, technicians at Jobin-Yvon, Inc. (JY) attempted to develop a device that would allow the generation of vapor phase elements and determine them concurrently with conventional nebulization of analytes in a cyclonic spray chamber. See http://icpoes.com/cma.htm. Reduced species are generated in a reservoir (created through the use of an elevated drain) located in the base of a modified gas-liquid separator, where excess hydrogen (caused by the use of a high concentration of acid, together with the reagent, sodium tetrahydroborate (III), also called sodium borohydride) sweeps out the vapors into the gas stream to be carried off to the excitation source. Using a novel flow system, and incorporating a focused microwave cavity for heating solutions, the JY technicians were able to report the determination of As, Bi, Ge, Hg, Pb, Sb, Se and Te. Id. While such methodology resulted in reported improvements in detection limits over conventional nebulization, the approach was marked by significant drawbacks, including the fact that the JY device: (1) requires high acid concentrations to be effective, (2) requires a specific protocol for the determination of elements, and (3) is designed specifically for JY optical spectrometers, whereas the present invention has broad applications to optical and mass spectrometers for elemental determinations.

A Japanese patent from 1989 (no. 1-170840) describes a system in which the non-nebulized component of a spray is led into a U-shape drain where hydrides are generated by the addition of a reducing agent. The aerosol part and the hydrides are delivered to the atomic spectrometer for determination. However, memory effects and sample volume control are difficult to maintain in this device.

A disclosure by Borgnon and Cadet, in a paper entitled, "Analyse des elements Hg, Se, As, Sn, Sb, et Bi en vapeur froide et hydrures par spectrométrie d'emission" Analusis, Vol. 16, pp. 77–80 (1988), is reported in U.S. Pat. No. 5,939,648 to represent a system that delivers hydrides and nebulized components. The Analusis paper, however, presents no claims for the determination of elements other than those delivered by vapor generation, since the nebulization of samples containing other elements results in excessive noise, and the device is described as having significant memory effects for several elements.

Similar work was disclosed by Li et al. in a paper entitled "Simultaneous determination of hydride and non-hydride forming elements by inductively coupled plasma atomic emission spectrometry," published in *Analytical Proceedings*, Vol. 29 pp. 438–439 (1992). The Li paper discloses a device in which hydrides are generated by mixing a solution of acid with the sample solution and then with a solution of sodium borohydride in a manifold (called a "chemifold" in this publication). The generated hydrides are swept into the spray chamber where a second part of the sample is introduced by nebulization. The two components are then delivered to the atomic spectrometry instrumentation. No further work was reported by the authors, who indicated that, "Certainly more experimental data are required before routine environmental analyses can be carried out with confidence with this method."

The foregoing inventions anticipate an invention, described in U.S. Pat. No. 5,939,648, assigned to Instruments S.A., Paris, France. In this device, hydride generation takes place within a spray chamber where the sample is introduced by nebulization. The sample portion that is not nebulized is collected in a modified drain where acid and sodium borohydride are introduced to generate the hydrides. In addition, the hydrogen, generated by the decomposition of the borohydride, is used to carry the hydrides into the gas phase, from where they are transported by a vector gas to the atomic spectrometer. For this device, the efficiency of transfer of the species to the gas phase would be reduced without the generation of hydrogen as an integral part of the operation.

Other inventors have used finely-divided gas bubbles that are generated by passage through a frit to separate the volatile species from the solution. See Brindle, Ian D. and Shaoguang Zheng, "A comparison of gas-liquid separators for the determination of mercury by cold-vapor sequential injection atomic absorption spectrometry", *Spectrochimica Acta Part B*, Vol. 51 at pp. 1777–1780 (1996). A problem with the frit type of device is that the noisiness of the signal increases as the concentration of the species to be measured increases. Vapor generation with simultaneous nebulization of solution has been previously used to enhance the signals generated in the plasma when a solution of easily ionized element, such as potassium, is nebulized simultaneously with the generation of vapor (Brindle, Ian D. and Xiao-chun Le, "Application of Signal Enhancement by Easily Ionized Elements in Hydride Generation Direct Current Plasma Atomic Emission Spectrometric Determination of Arsenic, Antimony, Germanium, Tin, and Lead," *Analytical Chemistry*, Vol. 61, pp. 1175–1178 (1989). A paper by Moor, et al. (*Journal of Analytical Atomic Spectrometry*, Vol. 15(2), pp. 143–49 (2000)) describes a system in which reagent and sample are mixed immediately prior to their being introduced into a spray chamber.

More conventional gas-liquid separators that use frits or other means to separate vapors from solutions for atomic spectrometry were not designed to operate simultaneously with a conventional nebulizer.

SUMMARY OF THE INVENTION

In light of the foregoing shortcomings and limitations in the prior art vapor generation and nebulization sample introduction techniques, a need exists for an improved combination of vapor generation and nebulization sample introduction processes that has a minimum of "cross-talk" between the vapor generation setup and the nebulizing operation. Such combination should possess, at the very least, all the positive attributes of both a gas-liquid separator and a spray chamber. Ideally, such combination would result in improved performance over both devices as compared to the results achieved by the separate operation of the devices.

It is the primary objective of the present invention to overcome the aforementioned shortcomings and limitations associated with the prior art by providing a new apparatus for introducing analyzing species in a laboratory sample. In accordance with this objective of the invention, there is provided an apparatus for performing such analysis comprising a system that combines the benefits of nebulization and vapor generation in a single device and that enables both the nebulization and vapor generation processes to be applied simultaneously to a single sample.

It is another objective of this invention to provide a system that will deliver either an aerosol or vapor phase species or both aerosol and vapor phase species together in a single device that is robust and easy to operate. An essential aspect of the present invention is the delivery of reagent solutions into an unconfined point gap, where vapor generation reaction can take place, and not within a confined tube, which could result in sputtering of solutions and gases into the device. The delivery of all solutions should be achieved while retaining the advantages of the two systems and without significantly compromising their sensitivities and detection capabilities. Furthermore, the device should not depend upon a high acid concentration, which is necessary in some devices, for the removal of the vapor phase species from the solution phase. In addition, the invention is particularly designed to eliminate any reservoir of solutions within the device that could result in interferences from components of the reacted or unreacted species introduced into the device.

One advantage of the present invention is that it can be used to determine elements in a sample separately as vapors (generated by a suitable reagent that will form a vapor with the element or compound that is to be determined) or in the form of an aerosol that is generated by a nebulizer, operating in the conventional mode for the determination of elements in solution. Another advantage of the present invention is that it can also be used with both the vapor generation and nebulization modes simultaneously. Yet another advantageous feature of this invention is that it allows operation in either the vapor generation or nebulization mode without needing to take apart the equipment to switch between modes. The invention is amenable to being interfaced with a flow-based system, but it is not required.

In accordance with one aspect of the present invention, referred to herein as the "dual mode," a determination can be made of the elements in a laboratory sample by the simultaneous application, in a single device, of both nebulization and vapor generation of such sample.

In accordance with another aspect of the present invention, referred to herein as the "single mode," a determination can be made of the elements in a laboratory sample introduced into a single piece of equipment, by application of either vapor generation or nebulization, but not both.

In accordance with yet another aspect of the present invention, a device is provided that is more efficient, yields lower detection limits and achieves greater reproducibility of results in determining a sample's elements than that provided by conventional vapor generation operations and conventional nebulization operations.

In accordance with still another aspect of the present invention, a device is provided that, when operated solely in the vapor generation mode, achieves a significant reduction in RSD as compared to that achieved by conventional vapor generation technologies, such as a frit-based gas-liquid separator. As noted above, frit-based gas-liquid separators are characterized by an increase in RSDs as the concentration of analyte increases, most likely due to frothing and bubbling within the gas-liquid separator. Such frothing and bubbling results in delivery of a relatively high amount of volatile analyte into the gas phase in an intermittent fashion as the bubbles burst, thereby giving rise to a variable signal whose excursions will increase as the concentration of the analyte increases.

By contrast, the present invention delivers a thin film of analyte solution and reductant onto a rough-surfaced cone, thereby ensuring both good mixing of the analyte solution and the reductant; as well as promoting exchange of volatile species with the gas which carries the analyte to the injector. Because the present invention keeps frothing and bubbling to a minimum and provides for smooth exchange with the vapor phase, RSDs fall as the concentration of analyte increases. In addition, the present invention reduces problems associated with a mixing "T," by introducing the sample and the reductant together at the point where the separation is started and by eliminating the pre-mixing of sample and reductant that is performed for most vapor generation systems using a mixing "T." Furthermore, because the reaction and separation occur within a few centimeters of the plasma within the MSIS device, there is little problem associated with the present invention with decomposition of the sample in the transfer line, such as has been observed with the decomposition of hydrogen selenide to elemental selenium in Tygon™ transfer lines.

In short, the present invention delivers excellent stability (low percent RSDs) for both vapor generation and for nebulization, and also gives low detection limits and corresponding improvement in sensitivity for the determination of a number of elements that can be generated in the vapor phase. In addition, the present invention eliminates transfer-line problems. Because the contact point between the sample and the reagent lies within the device, transit time is reduced which, in turn, enhances the transport efficiency of conventional and unstable species to the excitation source while keeping undesirable carryover to a minimum.

These and other objects, aspects and features of the present invention may be realized by the provision of an apparatus comprising a combined spray chamber/gas-liquid separator for use in atomic spectrometry which enables a laboratory sample to be simultaneously subjected to nebulization and vapor generation processes.

As will be appreciated by one of ordinary skill in the art, an apparatus according to the invention may be suitable for use in any field or industry requiring the processing of a material in a treatment vessel. Accordingly, the present invention should not be viewed as limited to any particular use or use in any particular industry. Additional objects, advantages and novel features of the present invention will be set forth in part in the description that follows, and in part will become apparent to those skilled in the art upon examination of the following or may be learned by practice of the invention. The objects and advantages of the invention may be realized and attained by means of the instrumentalities and combinations particularly pointed out in the appended claims.

BRIEF DESCRIPTION OF THE DRAWINGS

The drawing figures depicts the present invention by way of example, not by way of limitations.

DETAILED DESCRIPTION OF THE INVENTION

Figure 1:
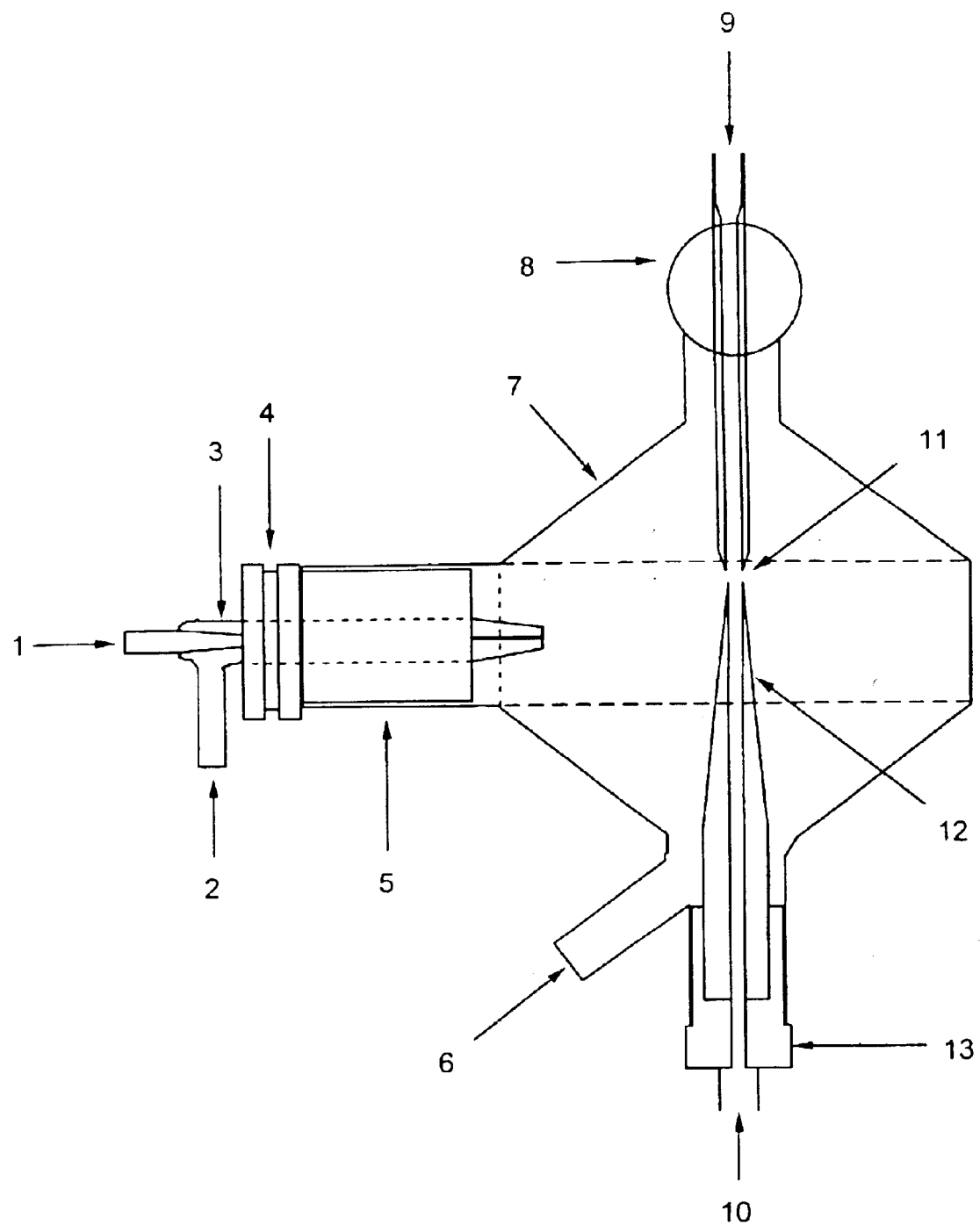
FIG. 1 is a side view of the Multimode Sample Introduction System according to the invention.
Figure 2:
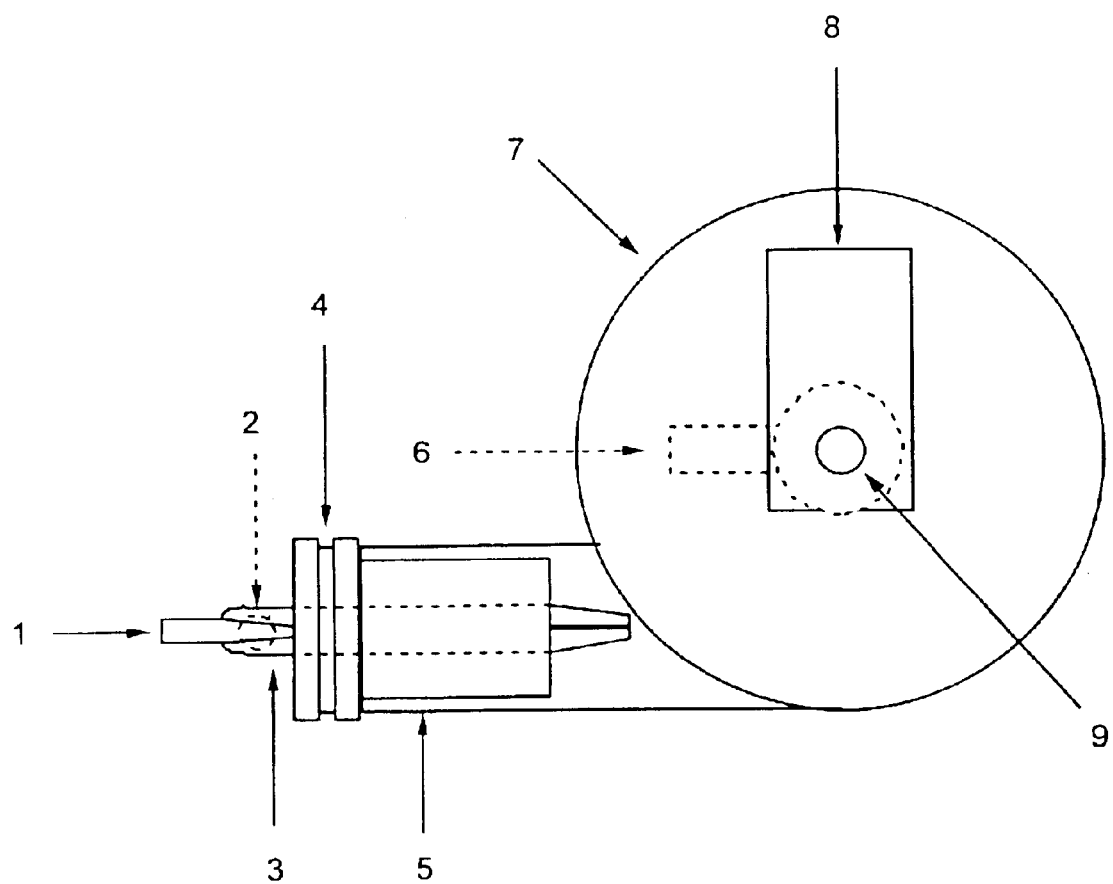
FIG. 2 is a top view of the Multimode Sample Introduction System according to the invention.
Figure 3:
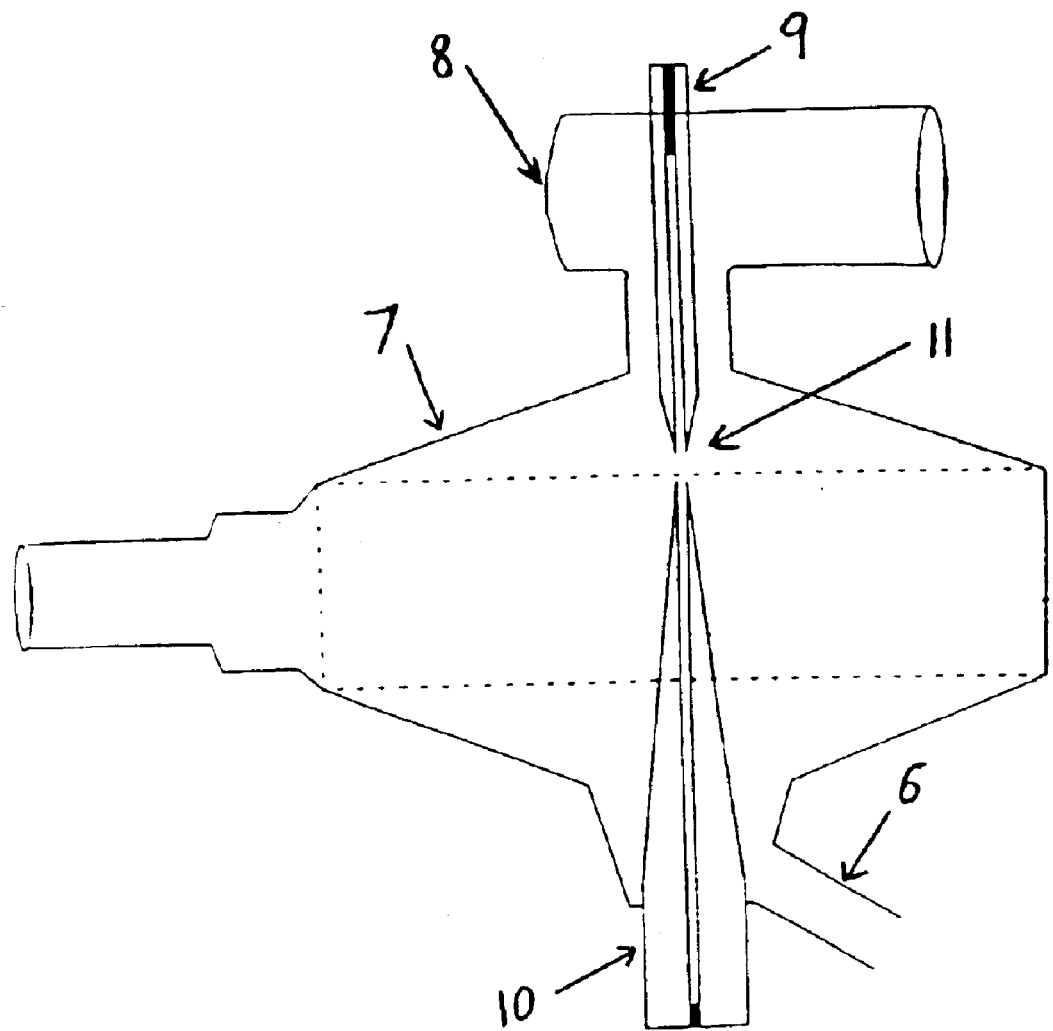
FIG. 3 is a cross-sectional view of the Multimode Sample Introduction System according to the invention, illustrating an enclosed chamber with two entry points for separate introduction of the sample and reagent (reductant) into the center of said chamber, a nebulizer port leading into the center of said chamber, and a plasma port exiting from said chamber.

In FIGS. 1–4, like reference numerals refer to the same or similar elements. Referring to FIG. 1, the device disclosed herein consists of a cyclonic spray chamber 7 that has been modified by the addition of two conical tubes, an upper, ground-glass, conical tube 9 and a lower tube 10, located vertically in the center of the spray chamber 7, with the two tubes 9 and 10 oriented at a 180-degree angle to each other. In the present invention, vapor generation takes place within the spray chamber 7, which also acts as a gas-liquid separator, and largely depends on the flow of gas to strip the analyte species and transfer them to the excitation source.

The two vertical delivery tubes 9 and 10 are placed centrally inside a cyclonic spray chamber 7, which is typically made from glass, with a gap 11 of 1–5 mm between the tubes. One tube is fitted to a pump to deliver the reagent; the second is fitted to a pump to deliver the sample; no preference is identified for which tube should receive which solution. The lower tube 10 is conical in shape as shown at reference numeral 12 and is diamond-ground or otherwise roughened to increase the surface area of the tube and thereby to permit better gas exchange between the mixed solutions and the transport gas. The tube is held in place by a fitting 13. Other spray chambers (double-pass, single pass, ultra-sonic, for example) can also incorporate the vapor generation apparatus.

A source of gas must be available that will act as a transport agent to extract the vapor-phase species and deliver them to the instrumentation for measurement. This gas source 2 may be supplied through a nebulizer 3, with entry point 1 being the location where solution to be nebulized is introduced into the nebulizer 3.

In the preferred embodiment shown, the spray chamber 7 is equipped with a means 3 of nebulizing solutions that are separated into a fine droplet part and a courser droplet part. The nebulizer 3 is inserted through entry point 5 of the spray chamber 7 through fitting 4. The fine droplets are delivered, together with the vapor phase species, to the atomic spectrometer. The coarser droplets coalesce and drain from the base of the spray chamber through a drain port 6. When the device is used exclusively for vapor generation, the two tubes 9 and 10 may be located inside a chamber with dimensions that will be required to accommodate the two tubes and to prevent any impedance of the flows of gas and solutions. The purpose of reducing these dimensions is to minimize the dead volume of the system, which can be advantageous for rapid clean-out and for flow-injection applications.

The bottom of the device is fitted with a drain port 6 that is constantly pumped, thereby ensuring that no reservoir of solution is built up inside the device. An upper exit port 8 at the top of the device provides a means by which the gas, vapor phase species and nebulized droplets are delivered to the atomic spectrometer.

The sample solution and the reagent are introduced separately from opposite directions into the center of the spray chamber 7; the solution flows down the surface of the upper tube 9 (to enhance gas-analyte exchange) and the stripping gas is introduced tangentially into the cyclonic chamber 7 via upper exit port 8. Many gas-liquid separators require that samples be prepared in high concentrations of acid to ensure a large production of hydrogen, which is used to transport the vapor-phase components to the excitation source. The location of the two introduction tubes 9 and 10 in the device further acts, in a secondary fashion, as a baffle to reduce the formation of water droplets in the injector. Vapor passes through the top of the device via the upper exit port 8, following a path concentric with the upper tube 9 to the excitation source. Waste from both vapor generation and nebulization is pumped from the base of the device via the drain port 6.

While the foregoing describes what are considered to be preferred embodiments of the present invention, it is understood that various modifications may be made thereto and that the invention may be implemented in various forms and embodiments, and that it may be applied in numerous applications, only some of which have been described herein. It is intended by the following claims to claim all such modifications and variations which fall within the true scope of the invention.

Figure 4:
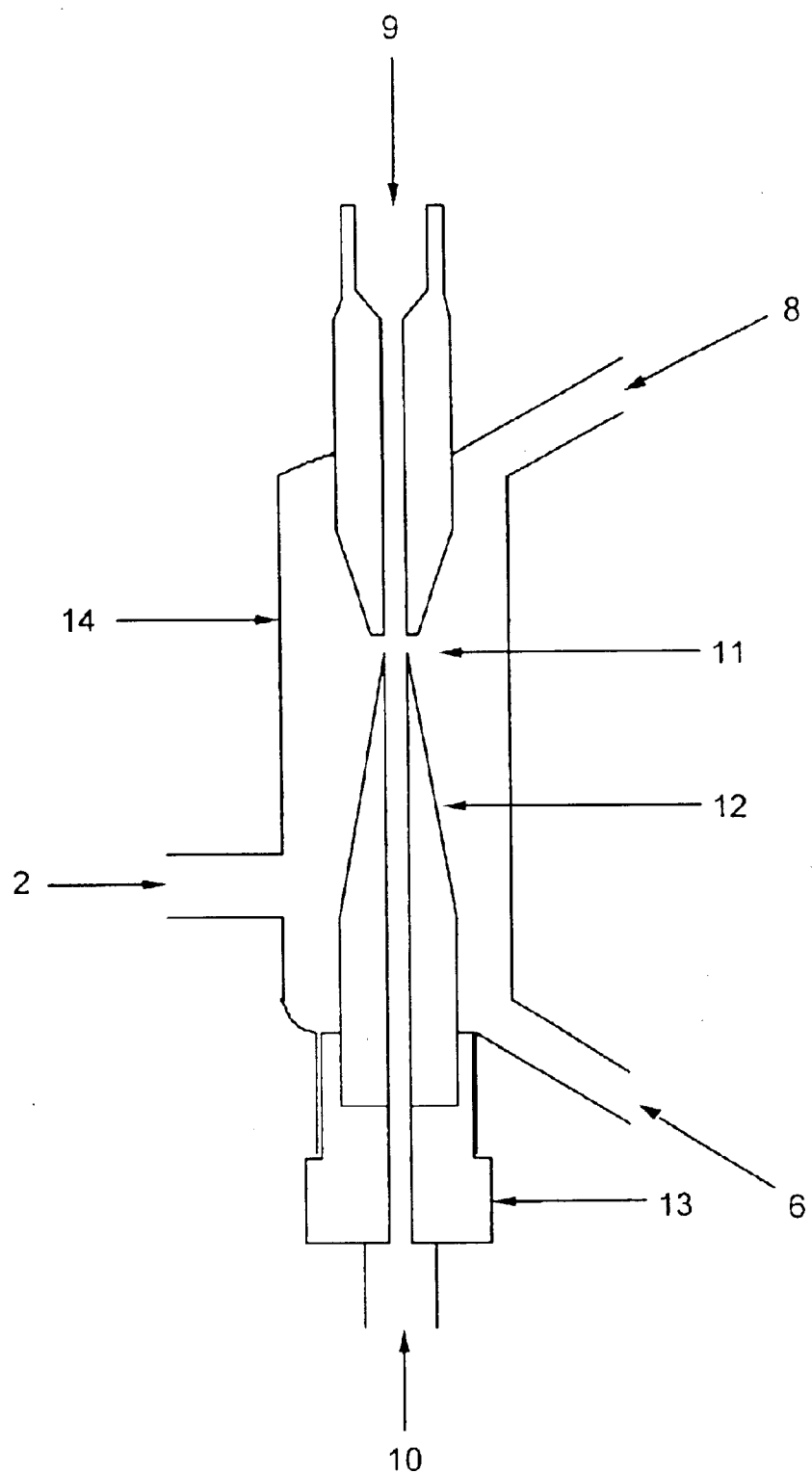
FIG. 4 is a side view of the delivery tubes component of the Multimode Sample Introduction System according to the invention.

Referring to FIG. 4, the invention is depicted as operating solely in the vapor generation mode, and therefore no nebulizer 1 is shown or used. In this mode, the spray chamber 7 in FIGS. 1–3 operates as a gas-liquid separator having a volume smaller than that of the spray chamber 7 in FIGS. 1–3. The outer shell 14 of the gas-liquid separator is depicted in FIG. 4.

What is claimed is:

1. An apparatus for introducing samples into a device used to determine one or more elements or compounds in such sample, comprising:

an enclosed spray chamber;

upper and lower conical tubes affixed to said spray chamber and oriented at a 180-degree angle to each other, and placed 1 to 5 mm apart from each other, with one end of each said tube terminating within the center portion of the spray chamber and the other end of each said tube protruding beyond the outside surface of the spray chamber;

a first cylindrical projection opening into a side of the spray chamber at an angle of 90 degrees to an imaginary axis joining said conical tubes;

a second cylindrical projection opening into a top surface of the spray chamber and oriented in parallel to the first cylindrical projection; and a third cylindrical projection with one end opening into a bottom surface of the spray chamber and the other end protruding downwardly beyond the outside surface of the spray chamber.

2. The apparatus of claim 1, wherein:

the upper and lower conical tubes provide the means to introduce a sample or a reagent into said spray chamber;

the first cylindrical projection accommodates a nebulizer that is equipped with a means of introducing a liquid sample as a fine spray into said spray chamber;

the second cylindrical projection provides the means to remove volatile analytes from said sample simultaneously with the introduction of said fine spray into the spray chamber through the first cylindrical projection; and the third cylindrical projection provides the means to drain waste materials from the spray chamber.

3. The apparatus of claim 2, wherein the nebulizer operates on a pneumatic, ultrasonic or other basis.

4. The apparatus of claim 2, wherein the introduction of the sample and reagent is performed on a continuous and regulated basis during analysis of the sample.

5. A method of introducing a liquid sample into a device to measure concentrations of elements in such sample by atomic spectrometry, in which:

a liquid sample and a reagent solution are introduced into an enclosed chamber through two capillary tubes;

said liquid and solution mix in an open space between the two tubes within said chamber, thereby forming a mixed solution;

the mixed solution flows down an outside surface of one of the tubes;

volatile species migrate from the mixed solution to a transfer gas;

the mixed solution is then immediately removed from said chamber through a drain means;

additional liquid sample is sprayed in droplets into the chamber via a nebulizer;

said droplets are carried by the transport gas into a means of separating fine droplets as an aerosol from coarser droplets;

said fine droplets are carried to an atomic spectrometer by the transport gas through a tube at a top of the chamber; and said coarser droplets coalesce to form a waste stream, which flows to the drain means and is immediately removed from the chamber.

* * * * *